United States Patent [19]
Müller et al.

[11] Patent Number: 5,849,751
[45] Date of Patent: *Dec. 15, 1998

[54] AMIDES AND SULPHONAMIDES OF BENZYLAMINES HAVING HETEROCYCLIC SUBSTITUENTS

[75] Inventors: Ulrich Müller, Wuppertal, Germany; Richard Connell, Trumbull, Conn.; Hilmar Bischoff, Wuppertal, Germany; Dirk Denzer, Wuppertal, Germany; Stefan Lohmer, Milan, Italy; Stefan Wohlfeil, Hilden, Germany; Rudi Grützmann, Solingen, Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 675,668

[22] Filed: Jul. 3, 1996

[30] Foreign Application Priority Data

Jul. 10, 1995 [DE] Germany .................. 195 25 028.1

[51] Int. Cl.$^6$ .................. A61K 31/44; C07D 471/04
[52] U.S. Cl. .................. 514/292; 514/256; 514/269; 514/274; 544/300; 544/310; 544/316; 544/319; 544/333; 546/87
[58] Field of Search .................. 546/87; 514/292, 514/256, 269, 274; 544/300, 310, 316, 319, 333

[56] References Cited

U.S. PATENT DOCUMENTS

| | | |
|---|---|---|
| 3,632,807 | 1/1972 | Maurer et al. . |
| 5,352,687 | 10/1994 | Müller et al. . |
| 5,395,840 | 3/1995 | Müller et al. . |
| 5,420,149 | 5/1995 | Müller et al. . |
| 5,478,836 | 12/1995 | Muller et al. .................. 514/292 |
| 5,527,809 | 6/1996 | Müller-Gliemann et al. . |
| 5,607,962 | 3/1997 | Müller-Gliemann et al. . |
| 5,646,162 | 7/1997 | Müller et al. . |
| 5,684,014 | 11/1997 | Müller et al. . |

FOREIGN PATENT DOCUMENTS 2098366  12/1993  Canada .

*Primary Examiner*—Patricia L. Morris
*Attorney, Agent, or Firm*—Sprung Kramer Schaefer & Briscoe

[57] ABSTRACT

Amides and sulphonamides of benzylamines having heterocyclic substituents are prepared by first converting the corresponding carboxylic acids into the corresponding amines and then substituting these on the amine nitrogen in a corresponding manner. The new amides and sulphonamides of benzylamines having heterocyclic substituents can be used as active compounds in medicaments, in particular in antiatherosclerotic medicaments.

9 Claims, No Drawings

AMIDES AND SULPHONAMIDES OF BENZYLAMINES HAVING HETEROCYCLIC SUBSTITUENTS

The present invention relates to amides and sulphonamides of benzylamines having heterocyclic substituents, processes for their preparation and their use as medicaments, in particular as antiatherosclerotic medicaments.

It is known that increased blood levels of triglycerides (hypertriglyceridaemia) and cholesterol (hypercholesterolaemia) are associated with the origin of atherosclerotic changes to the vascular walls and coronary heart diseases.

A significantly increased risk of the development of coronary heart diseases moreover exists if these two risk factors occur in combination, which in turn is accompanied by excessive production of apolipoprotein B-100. There is therefore still a great need for providing active medicaments for combating atherosclerosis and coronary heart diseases.

The present invention relates to amides and sulphonamides of benzylamines having heterocyclic substituents, of the general formula (I)

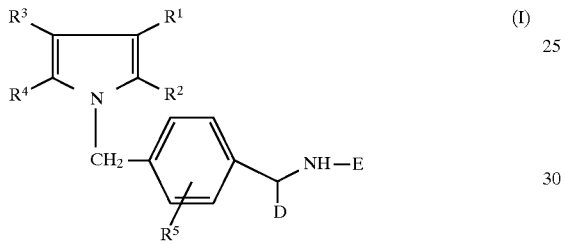

in which
$R^1$ and $R^2$, including the double bond joining them, together form a phenyl or pyridyl
$R^3$ and $R^4$, including the double bond joining them, together form a phenyl ring or a 4- to 8-membered cycloalkene radical,
   wherein all the ring systems mentioned under $R^1/R^2$ and $R^3/R^4$ are optionally substituted up to 3 times in an identical or different manner by halogen, trifluoromethyl, carboxyl, hydroxyl or straight-chain or branched alkoxy or alkoxycarbonyl having in each case up to 6 carbon atoms or by straight-chain or branched alkyl having up to 6 carbon atoms, which in its turn can be substituted by hydroxyl or by straight-chain or branched alkoxy having up to 4 carbon atoms,
$R^5$ represents hydrogen, halogen, nitro, hydroxyl, trifluoromethyl, trifluoromethoxy, straight-chain or branched alkyl, alkoxy or alkoxycarbonyl having in each case up to 6 carbon atoms, cyano or carboxyl,
D represents hydrogen or cycloalkyl having 4 to 8 carbon atoms, or represents straight-chain or branched alkyl having up to 8 carbon atoms,
E represents hydrogen, or represents a radical of the formula

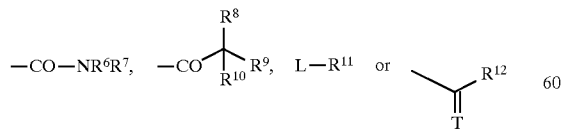

in which
$R^6$ and $R^7$ are identical or different and denote hydrogen, phenyl or straight-chain or branched alkyl having up to 6 carbon atoms, $R^8$ denotes hydrogen, straight-chain or branched alkyl having up to 6 carbon atoms, phenyl or a 5- to 7-membered saturated or unsaturated hetero- cyclic radical having up to 3 heteroatoms from the series consisting of S, N and/or O,
   wherein the cyclic radicals are optionally substituted up to 3 times in an identical or different manner by nitro, carboxyl, halogen or cyano or by straight-chain or branched alkoxycarbonyl having up to 6 carbon atoms or by straight-chain or branched alkyl having up to 6 carbon atoms, which is optionally substituted by hydroxyl or carboxyl or by straight-chain or branch ed alkoxy or alkoxycarbonyl having in each case up to 6 carbon atoms, and/or the cyclic radicals are optionally substituted by a group of the formula —$OR^{13}$,
   wherein
   $R^{13}$ represents hydrogen or straight-chain or branched alkyl or alkenyl having in each case up to 6 carbon atoms,
$R^9$ denotes carboxyl, hydroxyl, straight-chain or branched alkoxycarbonyl having up to 6 carbon atoms or a group of the formula —$CH_2OH$— or —O—CO—$R^{14}$,
   wherein
   $R^{14}$ represents straight-chain or branched alkyl having up to 6 carbon atoms,
$R^{10}$ denotes hydrogen,
or
$R^9$ and $R^{10}$ together form a radical of the formula =O or =N—$R^{15}$,
   wherein
   $R^{15}$ represents hydroxyl, straight-chain or branched alkoxy having up to 6 carbon atoms or a radical of the formula —NH—CO—$NH_2$ or —NH—CS—$NH_2$,
L denotes a group —$SO_2$— or —CO—,
$R^{11}$ denotes phenyl or a 5- to 7-membered aromatic heterocyclic radical having up to 3 heteroatoms from the series consisting of S, N and/or O, or denotes straight-chain or branched alkyl having up to 6 carbon atoms, which is optionally substituted by phenyl or by a 5- to 7-membered aromatic heterocyclic radical having up to 3 heteroatoms from the series consisting of S, N and/or O, wherein all the ring systems are optionally substituted up to 3 times in an identical or different manner by hydroxyl, phenoxy or halogen or by straight-chain or branched alkyl or alkoxy having in each case up to 5 carbon atoms,
T denotes an oxygen or sulphur atom and
$R^{12}$ denotes phenoxy, phenylthio or straight-chain or branched alkoxy having up to 6 carbon atoms,
and salts thereof.

The amides and sulphonamides according to the invention of benzylamines having heterocyclic substituents can also be in the form of their salts. Salts with organic or inorganic bases or acids may be mentioned here in general.

Physiologically acceptable salts are preferred in the context of the present invention.

Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphtha-lenedisulphonic acid, acetic acid, propionic acid, lactic acid, tartaric acid, citric acid, fumaric acid, maleic acid or benzoic acid.

Physiologically acceptable salts can likewise be metal or ammonium salts of the compounds according to the invention which have a free carboxyl group. Particularly preferred salts are, for example, sodium, potassium, magnesium or calcium salts, as well as ammonium salts which are derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine.

In the context of the invention, the cyclic radical ($R^3/R^4$), including the double bond of the basic skeleton, in general represent a 5- to 8-membered, preferably 5- to 7-membered, hydrocarbon radical, such as, for example, a phenyl, cyclopentene, cyclohexene, cycloheptene or cyclooctene radical. The cyclopentene, cyclohexene, cycloheptene and the phenyl radical are preferred.

A heterocyclic radical in the context of the invention in general represents a saturated or unsaturated 5- to 7-membered, preferably 5- to 6-membered, heterocyclic radical which can contain up to 3 heteroatoms from the series consisting of S, N and/or O. Examples which may be mentioned are: pyridyl, thienyl, furyl, pyrrolyl, thiazolyl, oxazolyl, imidazolyl, morpholinyl or piperidyl. Pyridyl and thienyl are preferred.

The compounds according to the invention can exist in stereoisomeric forms which either behave as mirror images (enantiomers) or do not behave as mirror images (diastereomers). The invention relates both to the enantiomers or diastereomers and to their particular mixtures. These mixtures of enantiomers and diastereomers can be separated into the stereoisomerically uniform constituents in a known manner.

In the case where E represents a radical of the formula =N—, the compounds according to the invention are also subject to E/Z isomerism. They can have the E or Z configuration or be in the form of an E/Z mixture.

Preferred compounds of the general formula (I) are those in which
$R^1$ and $R^2$, including the double bond joining them, together form a phenyl or pyridyl ring,
$R^3$ and $R^4$, including the double bond joining them, together form a phenyl ring or a cyclopentene, cyclohexene, cycloheptene or cyclooctene radical, wherein all the ring systems mentioned under $R^1/R^2$ and $R^3/R^4$ are optionally substituted up to twice in an identical or different manner by fluorine, chlorine, bromine, trifluoromethyl, carboxyl, hydroxyl or straight-chain or branched alkoxy or alkoxycarbonyl having in each case up to 4 carbon atoms or by straight-chain or branched alkyl having up to 4 carbon atoms, which in its turn can be substituted by hydroxyl or by straight-chain or branched alkoxy having up to 3 carbon atoms, $R^5$ represents hydrogen, fluorine, chlorine, bromine, trifluoromethyl, carboxyl or straight-chain or branched alkyl, alkoxy or alkoxycarbonyl having in each case up to 4 carbon atoms,
D represents hydrogen, cyclobutyl, cyclopentyl, cyclohexyl, cycloheptyl or cyclooctyl, or represents straight-chain or branched alkyl having up to 7 carbon atoms, E represents hydrogen, or represents a radical of the formula

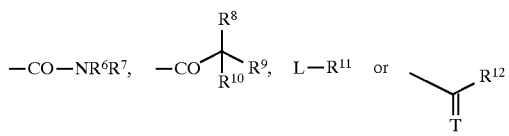

in which
$R^6$ and $R^7$ are identical or different and denote hydrogen, phenyl or straight-chain or branched alkyl having up to 6 carbon atoms,
$R^8$ denotes hydrogen, straight-chain or branched alkyl having up to 6 carbon atoms, phenyl, pyridyl, furyl, thienyl or imidazolyl, which are optionally substituted up to twice in an identical or different manner by nitro, carboxyl, fluorine, chlorine, bromine or cyano, by straight-chain or branched alkoxycarbonyl having up to 4 carbon atoms or by straight-chain or branched alkyl having up to 5 carbon atoms, which is optionally substituted by hydroxyl, carboxyl or by straight-chain or branched alkoxy or alkoxycarbonyl having in each case up to 5 carbon atoms, and/or the cyclic radicals are optionally substituted by a group of the formula —$OR^{13}$,
wherein
$R^{13}$ represents hydrogen or straight-chain or branched alkyl or alkenyl having in each case up to 4 carbon atoms,
$R^9$ denotes carboxyl, hydroxyl, straight-chain or branched alkoxycarbonyl having up to 4 carbon atoms or a group of the formula —$CH_2OH$ or —O—CO—$R^{14}$,
wherein
$R^{14}$ represents straight-chain or branched alkyl having up to 4 carbon atoms,
$R^{10}$ denotes hydrogen,
or
$R^9$ and $R^{10}$ together form a radical of the formula =O or =N—$R^{15}$,
wherein
$R^{15}$ represents hydroxyl, straight-chain or branched alkoxy having up to 4 carbon atoms or a radical of the formula —NH—CO—$NH_2$ or —NH—CS—$NH_2$,
L denotes a group —$SO_2$— or —CO,
$R^{11}$ denotes phenyl, pyridyl, thienyl, furyl or pyrimidyl or straight-chain or branched alkyl having up to 4 carbon atoms, which is optionally substituted by pyridyl, thienyl, furyl or pyrimidyl, wherein all the ring systems are optionally substituted up to twice in an identical or different manner by hydroxyl, phenoxy, fluorine, chlorine or bromine or by straight-chain or branched alkyl or alkoxy having in each case up to 4 carbon atoms,
T denotes a sulphur or oxygen atom and
$R^{12}$ denotes phenoxy, phenylthio or straight-chain or branched alkoxy having up to 4 carbon atoms,
and salts thereof Particularly preferred compounds of the general formula (I) are those
in which
$R^1$ and $R^2$, including the double bond joining them, together form a phenyl or pyridyl ring,
$R^3$ and $R^4$, including the double bond joining them, together form a phenyl ring or a cyclopentene, cyclohexene, cycloheptene or cyclooctene radical, wherein all the ring systems mentioned under $R^1/R^2$ and $R^3/R^4$ are optionally substituted up to twice in an identical or different manner by fluorine, chlorine, bromine, trifluoromethyl, carboxyl or hydroxyl, by straight-chain or branched alkoxy or alkoxycarbonyl having in each case up to 3 carbon atoms or by straight-chain or branched alkyl having up to 3 carbon atoms, which in its turn can be substituted by hydroxyl, methoxy or ethoxy, $R^5$ represents hydrogen, fluorine, chlorine, bromine, trifluoromethyl, trifluoro- methoxy or methyl, D represents hydrogen, cyclopentyl, cyclohexyl, cycloheptyl or cyclooctyl, or represents straight-chain or branched alkyl having up to 6 carbon atoms, E represents hydrogen, or represents a radical of the formula

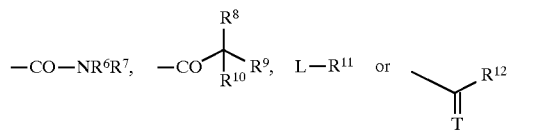

in which $R^6$ and $R^7$ are identical or different and denote hydrogen, phenyl or straight-chain or branched alkyl having up to 6 carbon atoms, $R^8$ denotes hydrogen, straight-chain or branched alkyl having up to 6 carbon atoms, phenyl, pyridyl or thienyl, which are optionally substituted up to twice in an identical or different manner by nitro, carboxyl, fluorine, chlorine, bromine or cyano, by straight-chain or branched alkoxycarbonyl having up to 3 carbon atoms or by straight-chain or branched alkyl having up to 4 carbon atoms, which is optionally substituted by hydroxyl or carboxyl or by straight-chain or branched alkoxy or alkoxycarbonyl having in each case up to 4 carbon atoms, and/or the cyclic radicals are optionally substituted by a group of the formula $—OR^{13}$, wherein $R^{13}$ represents hydrogen or straight-chain or branched alkyl or alkenyl having in each case up to 3 carbon atoms, $R^9$ denotes carboxyl, hydroxyl, straight-chain or branched alkoxycarbonyl having up to 3 carbon atoms or a group of the formula $—CH_2OH$ or $—O—CO—R^{14}$, in which $R^{14}$ represents straight-chain or branched alkyl having up to 3 carbon atoms, $R^{10}$ denotes hydrogen, or $R^9$ and $R^{10}$ together form a radical of the formula $=O$ or $=N—R^{15}$, wherein $R^{15}$ denotes hydroxyl, straight-chain or branched alkoxy having up to 3 carbon atoms or a radical of the formula $—NH—CO—NH_2$ or $—NH—CS—NH_2$, L denotes a radical of the formula $—SO_2$ or $—CO$, $R^{11}$ denotes phenyl, pyridyl or thienyl or straight-chain or branched alkyl having up to 3 carbon atoms, which is optionally substituted by phenyl, pyridyl or thienyl, wherein all the ring systems are optionally substituted up to twice in an identical or different manner by hydroxyl, phenoxy, fluorine, chlorine or bromine or by straight-chain or branched alkyl or alkoxy having in each case up to 3 carbon atoms, T denotes a sulphur or oxygen atom and $R^{12}$ denotes phenoxy, phenylthio or straight-chain or branched alkoxy having up to 3 carbon atoms, and salts thereof $R^1$ and $R^2$, including the double bond, especially preferably form a pyridyl ring. $R^3$ and $R^4$, including the double bond, particularly preferably form a phenyl ring.

$R^3$ and $R^4$, including the double bond, likewise preferably form a cyclopentene or -hexene ring.

A process has furthermore been found for the preparation of the compounds of the general formula (I) according to the invention, characterized in that carboxylic acids of the general formula (II)

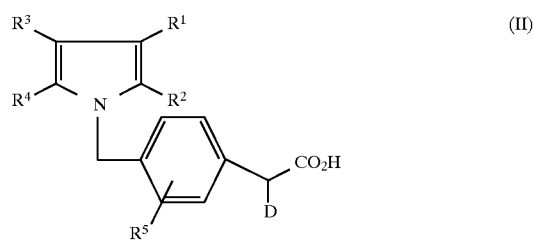

in which $R^1$, $R^2$, $R^3$, $R^4$, $R^5$ and D have the meaning given, are first converted, by reaction with phosphoric acid diphenyl ester azide in inert solvents and in the presence of a base, into the amines of the general formula (Ia)

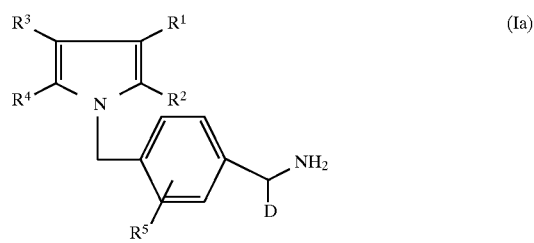

in which $R^1$, $R^2$, $R^3$, $R^4$, $R^5$ and D have the meaning given, and these are then reacted with compounds of the general formula (III)

in which $E^1$ has the abovementioned meaning of E, but does not represent hydrogen, and X represents hydroxyl or halogen, depending on the radicals mentioned under E, in inert organic solvents, if appropriate in the presence of a base and/or of auxiliaries, and if appropriate the products are derivatized or varied.

The processes according to the invention can be illustrated by way of example by the following equation:

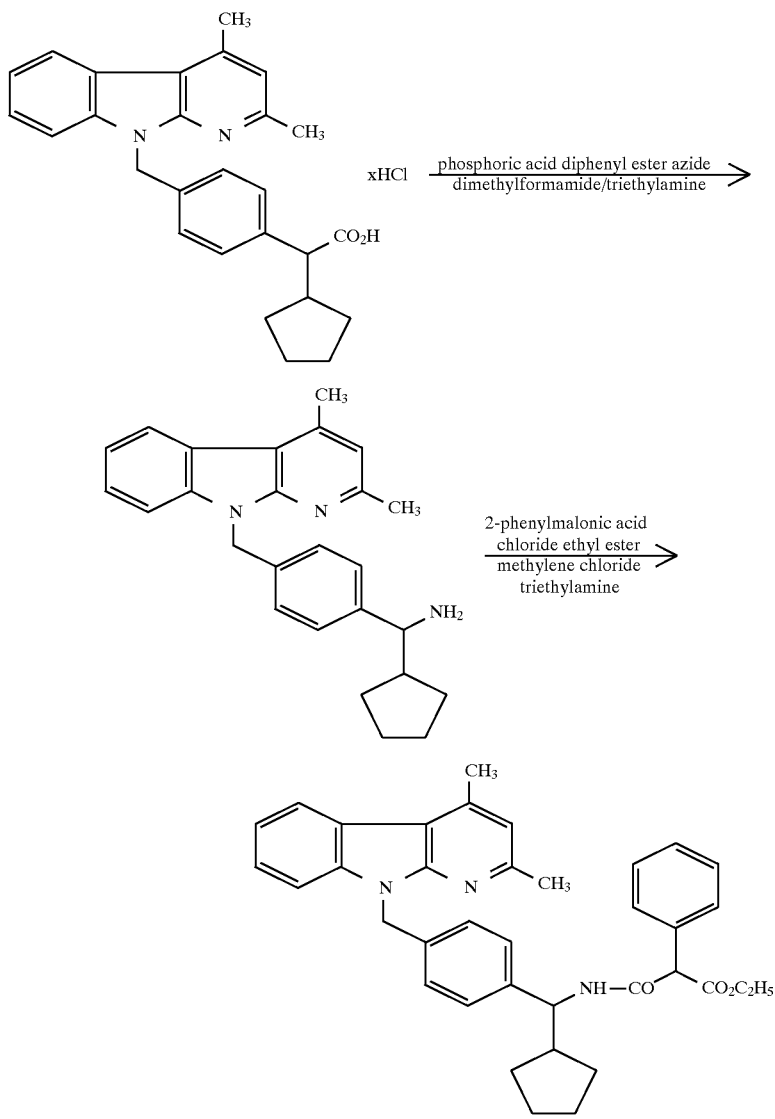

Suitable solvents for the individual steps here are inert organic solvents which do not change under the reaction conditions. These include ethers, such as diethyl ether or tetrahydrofuran, halohydrocarbons, such as methylene chloride, chloroform, carbo-tetrachloride, 1,2-dichloroethane, trichloroethane, tetrachloroethane or trichloroethylene, hydrocarbons, such as benzene, xylene, toluene, hexane, cyclohexane or petroleurn fractions, nitromethane, dimethylformamide, acetone, acetonitrile or hexamethylphosphoric acid triamide.

It is also possible to employ mixtures of the solvents. Methylene chloride, tetrahydro- furan, acetone or dimethylformamide is particularly preferred.

Bases which can be employed for the process according to the invention are in general inorganic or organic bases. These include, preferably, alkali metal hydroxides, such as, for example, sodium hydroxide or potassium hydroxide, alkaline earth metal hydroxides, such as, for example, barium hydroxide, alkali metal carbonates, such as sodium carbonate or potassium carbonate, alkaline earth metal carbonates, such as calcium carbonate, or alkali metal or alkaline earth metal alcoholates, such as sodium or potassium methanolate, sodium or potassium ethanolate or potassium tert-butylate, or organic amines (trialkyl($C_1$–$C_6$) amines), such as triethylamine, or heterocyclic compounds, such as 1,4-diazabicyclo[2.2.2]octane (DABCO), 1,8-diazabicyclo-[5.4.0]undec-7-ene (DBU), pyridine, diaminopyridine, methylpiperidine or morpholine. It is also possible to employ alkali metals, such as sodium, and hydrides thereof, such as sodium hydride, as bases. Sodium carbonate and potassium carbonate and triethylamine are preferred.

The base is employed in an amount of 1 mol to 5 mol, preferably 1 mol to 3 mol, per mole of the compound of the general formula (II).

The reaction is in general carried out in a temperature range from 0° C. to 150° C., preferably from +20° C. to +110° C.

The reaction can be carried out under normal or increased or under reduced pressure (for example 0.5 to 5 bar). It is in general carried out under normal pressure.

If appropriate, the amidation can also proceed via the activated stage of the acid halides, which can be prepared from the corresponding acids by reaction with thionyl chloride, phosphorus trichloride, phosphorus pentachloride, phosphorus tribromide or oxalyl chloride.

Where appropriate, the abovementioned bases can also be employed as acid-binding auxiliaries for the amidation.

Suitable auxiliaries are likewise dehydrating reagents. These include, for example, carbodiimides, such as diisopropylcarbodiimide, dicyclohexylcarbodiimide or N-(3-dimethylaminopropyl)-N'-ethylcarbodiimide hydrochloride, or carbonyl compounds, such as carbonyldiimidazole, or 1,2-oxazolium compounds, such as 2-ethyl-5-phenyl-1,2-oxazolium 3-sulphonate, or propanephosphoric acid anhydride or isobutyl chloroformate or benzotriazolyloxy-tris-(dimethylamino)phosphonium hexyl-fluorophosphate or phosphonic acid diphenyl ester amide or methane-sulphonyl chloride, if appropriate in the presence of bases, such as triethylamine or N-ethylmorpholine or N-methylpiperidine or dicyclohexyl-carbodiimide and N-hydroxysuccinimide.

The acid-binding agents and dehydrating reagents are in general employed in an amount of 0.5 to 3 mol, preferably 1 to 1.5 mol, per mole of the corresponding carboxylic acids.

The variation of functional groups, such as, for example, hydrolysis, esterification and reduction, and the separation of isomers and salt formation are carried out by customary methods.

The compounds of the general formula (III) are known per se or can be prepared by customary methods.

The compounds of the general formula (Ia) are new and can be prepared as described above.

The carboxylic acids of the general formula (II) are new and can be prepared by a process in which compounds of the general formula (IV)

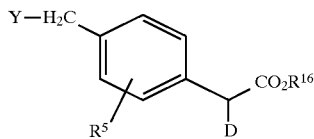

in which
D and $R^5$ have the meaning given,
Y represents a typical leaving group, such as, for example, chlorine, bromine, iodine, tosylate or mesylate, preferably bromine,
and
$R^{16}$ represents straight-chain or branched alkyl having up to 4 carbon atoms, are reacted with compounds of the general formula (V)

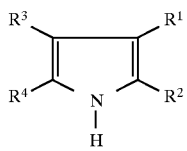

in which
$R^1$, $R^2$, $R^3$ and $R^4$ have the meaning given, in inert solvents, if appropriate in the presence of a base.

Suitable solvents for the process are customary organic solvents which do not change under the reaction conditions. These include, preferably, ethers, such as diethyl ether, dioxane, tetrahydrofuran or glycol dimethyl ether, or hydrocarbons, such as benzene, toluene, xylene, hexane, cyclohexane or petroleum fractions, or halogenated hydrocarbons, such as methylene chloride, chloroform, carbon tetrachloride, dichloroethylene, trichloroethylene or chlorobenzene, or ethyl acetate, triethylamine, pyridine, dimethyl sulphoxide, dimethylformamide, hexamethylphosphoric triamide, acetonitrile, acetone or nitromethane. It is also possible to use mixtures of the solvents mentioned. Dimethylformamide and tetrahydrofuran are preferred.

Bases which can be employed for the process according to the invention are in general inorganic or organic bases. These include, preferably, alkali metal hydroxides, such as, for example, sodium hydroxide or potassium hydroxide, alkaline earth metal hydroxides, such as, for example, barium hydroxide, alkali metal carbonates, such as sodium carbonate or potassium carbonate, alkaline earth metal carbonates, such as calcium carbonate, or alkali metal or alkaline earth metal alcoholates, such as sodium or potassium methanolate, sodium or potassium ethanolate or potassium tert-butylate, or organic amines (trialkyl($C_1$–$C_6$) amines), such as triethylamine, or heterocyclic compounds, such as 1,4-diazabicyclo[2.2.2]octane (DABCO), 1,8-diazabicyclo-[5.4.0]undec-7-ene (DBU), pyridine, diaminopyridine, methylpiperidine or morpholine. It is also possible to employ alkali metals, such as sodium, or hydrides thereof, such as sodium hydride, as bases. Sodium hydride, potassium carbonate, triethylamine, pyridine and potassium tert-butylate, DBU or DABCO are preferred.

The base is in general employed in an amount of 0.05 mol to 10 mol, preferably 1 mol to 2 mol, per mole of the compound of the formula (IV).

The process according to the invention is in general carried out in a temperature range from –30° C. to +100° C., preferably from –10° C. to +60° C.

The process according to the invention is in general carried out under normal pressure. However, it is also possible to carry out the process under increased pressure or under reduced pressure (for example in a range from 0.5 to 5 bar).

The compounds of the general formula (IV) are known or can be prepared by methods analogous to known methods.

The compounds of the general formula (V) are known or can be prepared by methods analogous to known methods.

The compounds of the general formula (I) and (Ia) according to the invention have an unforeseeable pharmacological action spectrum.

They can be used as active compounds in medicaments for reducing changes in the walls of vessels and for treatment of coronary heart diseases, cardiac insufficiency, disturbances in cerebral performance, ischaemic cerebral diseases, apoplexy, circulatory disturbances, microcirculation disturbances and thromboses.

The proliferation of smooth muscle cells furthermore plays a decisive role in the occlusion of vessels. The compounds according to the invention are capable of inhibiting this proliferation and therefore of preventing atherosclerotic processes. The compounds according to the invention are distinguished by a lowering of the apoB-100-associated lipoproteins (VLDL and its degradation products, such as, for example, LDL), apoB-100, triglycerides and cholesterol. They therefore have valuable pharmacological properties which are superior compared with the prior art.

Surprisingly, the action of the compounds according to the invention initially consists of a reduction or complete inhibition of the formation and/or release of apoB-100-associated lipoproteins from liver cells, which results in a lowering of the plasma VLDL level. This VLDL level must be accompanied by a lowering in the plasma levels of apoB-100, LDL, triglycerides and cholesterol; several of the abovementioned risk factors which participate in changes to the vessel walls are thus lowered at the same time.

The compounds according to the invention can therefore be employed for prevention and treatment of atherosclerosis, obesity, pancreatitis and constipation.

1. Inhibition of the release of apoB-100-associated lipoproteins

The test for detection of the inhibition of the release of apoB-100-associated lipoproteins from liver cells was carried out in vitro with cultured liver cells, preferably with cells of the human line HepG2. These cells are cultured under standard conditions in a medium for the culture of eukaryotic cells, preferably in RPMI 1640 with 10% foetal calf serum. HepG2 cells synthesize and secrete into the culture supernatant apoB-100-associated lipoprotein particles, which in principle are similar in structure to the VLDL and LDL particles to be found in plasma.

These particles can be detected with an immunoassay for human LDL. This immunoassay is carried out with antibodies which had been induced in the rabbit against human LDL under standard conditions. The anti-LDL antibodies (rab-anti-LDL- ab) were purified by affinity chromatography on an immunosorbent with human LDL. These purified rab-anti-LDL-ab are adsorbed onto the surface of a plastic. This adsorption is expediently carried out onto the plastic surface of microtitre plates with 96 wells, preferably on MaxiSorp plates. If apoB-100-associated particles are present in the supernatant of Hep-G2 cells, these can bind to the insolubilized rab-anti-LDL-ab, and an immune complex bonded to the plastic surface is formed. Non-bound proteins are removed by washing. The immune complex on the plastic surface is detected with monoclonal antibodies which have been induced against human LDL and purified under standard conditions. These antibodies were conjugated with the enzyme peroxidase. Peroxidase converts the colourless substrate TMB into a coloured product in the presence of $H_2O_2$. After acidification of the reaction mixture with $H_2SO_4$, the specific adsorption of light at 450 nm is determined, this being a measure of the amount of apoB-100-associated particles which have been secreted into the culture supernatant by the HepG2 cells.

Surprisingly, the compounds according to the invention inhibit the release of apoB- 100-associated particles. The $IC_{50}$ value indicates the concentration of substance at which the adsorption of light is inhibited by 50% compared with the control (solvent control without substance).

| Example No. | $IC_{50}$ [$10^{-9}$ mol/l] |
|---|---|
| 1 | >2000 |
| 3 | 460 |
| 4 | 34 |
| 5 | 38 |
| 11 | 250 |
| 18 | 39 |
| 24 | 300 |

2. Determination of the VLDL secretion in vivo on the hamster

The effect of the test substances on VLDL secretion in vivo is investigated on the hamster. For this, after premedication with atropine (83 mg/kg s.c.), golden hamsters are anaesthetized with Ketavet (83 mg/kg s.c.) and Nembutal (50 mg/kg i.p.). When the animals have become free from reflexes, the v. jugularis is exposed and a cannula inserted. 0.25 ml/kg of a 20% strength solution of Triton WR-1339 in physiological sodium chloride solution is then administered. This detergent inhibits lipoprotein lipase and thus leads to an increase in the triglyceride level because of an absence of catabolism of secreted VLDL particles. This increase in triglycerides can be used as a measure of the VLDL secretion rate. Blood is sampled from the animals by puncture of the retroorbital venous plexus before and one and two hours after administration of the detergent. The blood is incubated for two hours at room temperature and then overnight at 4° C. in order to conclude coagulation completely. Thereafter, it is centrifuged at 10,000 g for 5 minutes. The triglyceride concentration is determined in the serum thus obtained with the aid of a modified commercially obtainable enzyme test (Merckotest® Triglyceride No. 14354). 100 µl of test reagent are added to 100 µl of serum in 96-well plates and the samples are incubated at room temperature for 10 minutes. The optical density is then determined at a wavelength of 492 nM in an automatic plate-reading apparatus (SLT-Spectra). Serum samples having an excessive triglyceride concentration are diluted with physiological sodium chloride solution. The triglyceride concentration contained in the samples is determined with the aid of a standard curve measured in parallel. In this model, test substances are administered either intravenously immediately before administration of the detergent or orally or subcutaneously before induction of the anaesthesia.

3. Inhibition of intestinal triglyceride absorption in vivo (rats)

The substances which are to be investigated for their inhibiting action on triglyceride absorption in vivo are administered orally to male Wistar rats having a body weight of between 170 and 230 g. For this purpose, the animals are divided into groups of 6 animals 18 hours before administration of the substance, and their food is then withdrawn. Drinking water is available to the animals ad libitum. The animals of the control groups are given an aqueous tragacanth suspension or a tragacanth suspensio n which contains olive oil. The tragacanth/olive oil suspension is prepared using an Ultra-Turrax. The substances to be investigated are suspended in a corresponding tragacanth/olive oil suspension, likewise using an Ultra-Turrax, directly before administration of the substance.

Blood is sampled from each rat by puncture of the rectroorbital venous plexus before the administration by stomach tube, in order to determine the basal serum triglyceride content. The tragacanth suspension, the tragacanth/olive oil suspensions without substance (control animals) or the substances suspended in a corresponding tragacanth/olive oil suspension are then administered to the fasting animals using a stomach tube. Further blood samples for determination of the postprandial increase in serum triglycerides are as a rule taken 1, 2 and 3 hours after the administration by stomach tube.

The blood samples are centrifuged and, after coagulation of the serum, the triglycerides are determined photometrically using an EPOS Analyzer 5060 (Eppendorf Gerätebau, Netheler & Hinz GmbH, Hamburg). The triglycerides are determined completely enzymatically using a commercially available UV test.

The postprandial increase in serum triglycerides is determined by subtraction of the triglyceride pre-value of each animal from its corresponding postprandial triglyceride concentrations (1, 2 and 3 hours after administration).

The average is taken of the differences (in mmol/l) at each point in time (1, 2 and 3 hours) in the groups, and the means of the increase in serum triglycerides ($\Delta TG$) of the animals treated with substance are compared with those of the animals given only the tragacanth/oil suspension.

The course of the serum triglycerides in the control animals given only tragacanth is also calculated. The effect of the substance at each point in time (1, 2 or 3 hours) is determined as follows and stated in $\Delta\%$ of the control loaded with oil.

$$\Delta\% \text{ increase in triglycerides} = \frac{\Delta TG_{substance} - \Delta TG_{tragacanth\ control}}{\Delta TG_{oil\ loading} - \Delta TG_{tragacanth\ control}} \times 100$$

Effect of 10 mg of test substance/kg of body weight p.o. on the increase in triglycerides ($\Delta\%$) 2 hours after a triglyceride loading in the serum of fasting rats. The increase in serum triglycerides of control animals loaded with fat, based on the serum triglyceride level of tragacanth control animals, corresponds to 100%. n=6 animals per group.

The statistical analysis is carried out with the Student's t-test after first checking the variances for homogeneity.

Substances which statistically significantly ($p<0.05$) reduce the postprandial increase in serum triglycerides by at least 30%, compared with that of the untreated control group, at a point in time are regarded as pharmacologically active.

4. Inhibition of VLDL secretion in vivo (rat) The action of the test substances on VLDL secretion is likewise investigated on the rat. For this, 500 mg/kg of body weight (2.5 mg/kg) of Triton WR-1339, dissolved in physiological sodium chloride solution, are administered intravenously into the tail vein of rats. Triton WR-1339 inhibits lipoprotein lipase and this leads to an increase in the triglyceride and cholesterol level by inhibition of VLDL catabolism. These increases can be used as a measure of the VLDL secretion rate.

Blood is sampled from the animals by puncture of the retroorbital venous plexus before and one and two hours after administration of the detergent. For coagulation, the blood is incubated at room temperature for 1 hour, and the serum is isolated by centrifugation at 10 000 g for 20 seconds. The triglycerides are then determined photometrically at a wavelength of 540 nm by means of a commercially available coupled enzyme test (Sigma Diagnostics®, No. 339). The measurement is carried out with the aid of an enzyme test, which is also coupled (Boehringer Mannheim®, No. 1442350), at a wavelength of 546 nm. Samples with triglyceride or cholesterol concentrations which exceed the measurement range of the methods are diluted with physiological sodium chloride solution. The particular serum concentrations are determined with the aid of standard series measured in parallel. Test substances are administered orally, intravenously or subcutaneously immediately after the Triton injection.

The invention furthermore relates to the combination of amides and sulphonamides of benzylamines having heterocyclic substituents, of the general formula (1), with a glucosidase and/or arylase inhibitor for treatment of familial hyperlipidaemias, obesity (adiposity) and diabetes mellitus. Glucosidase and/or arylase inhibitors in the context of the invention are, for example, acarbose, adiposine, voglibose (AO-128), miglitol, emiglitate, MDL-25637, camiglibase (MDL-73945), tendamistete, AI-3688, treslatine, pradimicin-Q and salboslatine. The combination of acarbose, miglitol, emiglitate or voglibose with one of the abovementioned compounds of the general formula (I) according to the invention is preferred.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should in each case be present here in a concentration of about 0.5 to 90% by weight of the total mixture, that is to say in amounts which are sufficient to achieve the stated dosage range.

The formulations are prepared, for example, by extending the active compounds with solvents and/or excipients, if appropriate using emulsifying agents and/or dispersing agents, and, for example, in the case where water is used as a diluent, organic solvents may be used as auxiliary solvents if appropriate.

Administration is carried out in the customary manner, preferably orally or parenterally, in particular perlingually or intravenously.

In the case of parenteral use, solutions of the active compound can be employed, using suitable liquid carrier materials.

In general, it has proved advantageous in the case of intravenous administration to administer amounts of about 0.001 to 1 mg/kg, preferably about 0.01 to 0.5 mg/kg of body weight, to achieve effective results, and in the case of oral administration the dosage is about 0.01 to 20 mg/kg, preferably 0.1 to 10 mg/kg of body weight.

Nevertheless, it may be necessary, where appropriate, to deviate from the amounts mentioned, and in particular to do so as a function of the body weight or the nature of the administration route, of the behaviour of the individual towards the medicament, of the nature of the formulation thereof and of the time or interval at which administration takes place. Thus, in some cases it may be sufficient to manage with less than the abovementioned minimum amount, while in other cases the upper limit mentioned must be exceeded. In the case of administration of relatively large amounts, it may be advisable to divide these into several individual doses over the course of the day.

Abbreviations Used

Ac=acetyl
Bn=benzyl
Bz=benzoyl
cDec=cyclodecyl
cDodec=cyclododecyl
cHept=cycloheptyl
cHex=cyclohexyl
cNon=cyclononyl
cOct=cyclooctyl
cPent=cyclopentyl
cPr=cyclopropyl
cUndec=cycloundecyl
DCC=dicyclohexylcarbodiimide
DDQ=2,3-dichloro-5,6-dicyano-1,4-benzoquinone
dia=diastereomer
DMAP=4-(N,N-dimethylamino)pyridine
DMF=N,N-dimethylformamide
DMSO=dimethylsulphoxide
ent=enantiomer
Et=ethyl
HOBT=1-hydroxy-1H-benzotriazole
iBu=isobutyl
iPr=isopropyl
Me=methyl
Mes=mesyl
NBS=N-bromosuccinimide
nBu=normal butyl
nPr=normal propyl
Ph=phenyl
PPA=polyphosphoric acid
pTol=paratolyl
pTos=paratosyl
rac=racemate
sBu=secondary butyl
tBu=tertiary butyl TFA=trifluoroacetic acid
THF=tetrahydrofuran
TMS=tetramethylsilane

| Solvent | Designation |
|---|---|
| Methylene chloride:ethanol = 20:1 | A |
| Methylene chloride:ethanol = 50:1 | B |
| Methylene chloride:ethanol = 100:1 | C |
| Petroleum ether:ethyl acetate = 1:1 | D |
| Methylene chloride:methanol = 50:1 | E |
| Petroleum ether:ethyl acetate = 5:1 | F |

Starting Compounds

EXAMPLE I

6-Chloro-2,4-lutidine (2-chloro-4,6-dimethyl-pyridine)

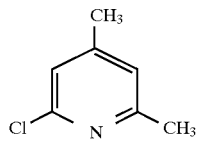

To prepare the title compound [US 36 32 807], 600 g (4.91 mol) of 6-amino-2,4-lutidine are dissolved in 2 l of methanol and the solution is saturated with hydrogen chloride gas at about 0° C. 1,307 l (9.82 mol) of isopentyl nitrite are added dropwise at an internal temperature below 10° C. (about 2.5 hours) and the mixture is left to stand thus for 15 hours, while warming to room temperature (about 25° C.). The solution is largely freed from the solvent in vacuo, 3 l of methylene chloride and 1.5 l of water are added and the pH is brought to 9.5 with concentrated aqueous ammonia solution, while cooling (<20° C.). The organic phase is separated off, dried with sodium sulphate and first concentrated in vacuo on a rotary evaporator and then distilled over a Vigreux column:

Fraction 1) boiling point=47°–49° C. (12 mmHg), 603 g

Fraction 2) boiling point=82°–85° C. (12 mmHg), 612 g (about 88% crude)

$R_f$=0.39 (petroleum ether: ethyl acetate=10:1)

The crude product, which can contain small amounts of 6-methoxy-2,4-lutidine, is further reacted without further purification.

EXAMPLE II

6-Hydrazino-2,4-lutidine (4,6-dimethyl-2-hydrazino-pyridine)

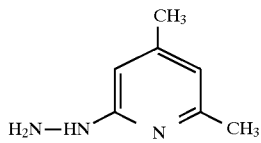

580 g (4.10 mol) of the compound from Example I are dissolved in 800 ml of diethylene glycol and the solution is stirred with 1050 ml of hydrazine hydrate at a bath temperature of about 140° C. for 48 hours. The cooled batch is poured onto 4.5 l of ether and 4.5 l of water and the organic phase is extracted twice with 2.3 l of methylene chloride each time. The combined organic phases are dried with sodium sulphate and evaporated in vacuo. 784 g of solvent-containing crude product which is further reacted without working up are obtained.

$R_f$=0.37 (methylene chloride: methanol=10:1)

EXAMPLE III 2,4-Dimethyl-5,6,7,8-tetrahydro-α-carboline

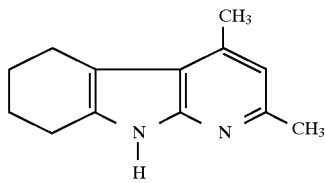

78 g (0.49 mol maximum) of the crude compound from Example II are reacted with 59 ml (0.56 mol) of cyclohexanone at room temperature (about 25° C.), during which the internal temperature rises. After 2 hours, the educt has disappeared (monitoring by thin layer chromatography; methylene chloride: methanol=10:1). The mixture is taken up in 40 ml of diethylene glycol and reacted under reflux, constituents which boil at a lower temperature than the solvent (for example water of reaction and excess cyclohexanone) being removed by distillation (water separator). After 3 hours, the intermediate hydrazine has disappeared (monitoring by thin layer chromatography; petroleum ether : ethyl acetate=1:1); the reaction mixture is cooled to room temperature and stirred with acetone. The precipitate obtained is filtered off with suction, rinsed with acetone and dried in vacuo (34.4 g). The mother liquors are largely freed from the solvent and treated with acetone again, a further 9.3 g of product being obtained (total yield over 3 stages: 43.7 g/0.22 mol/47%). Melting point: 248° C. (uncorrected) $R_f$=0.41 (methylene chloride: ethanol=20: 1)

EXAMPLE IV 2,4-Dimethyl-α-carboline

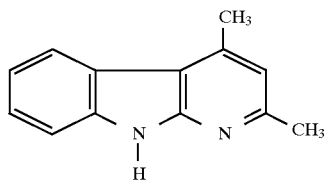

100 g (499 mmol) of the compound from Example III are reacted with 164 ml (1 mol) of diethyl fumarate over 52 g of palladium (5% on charcoal) in 700 ml of diethylene glycol under reflux. At the high internal temperature, a small amount of ethanol distils off (use a water separator if appropriate). After about 8 hours, the educt has disappeared (monitoring by thin layer chromatography; petroleum ether: ethyl acetate=1:1, detection in an iodine chamber). 3 l of acetone are added to the cooled mixture, the mixture is boiled up and filtered hot with suction over a clarifying filter (Seitz), and the residue is rinsed with 1 l of hot acetone. On cooling, a precipitate separates out, which, after filtration with suction, rinsing with cold acetone and drying in vacuo, gives 58.3 g of product. The mother liquor is largely freed from acetone in vacuo, the precipitate which separates out being worked up as above (9.4 g). The filtrate is again freed from acetone; after addition of n-pentane, product precipitates again (3.1 g/working up, see above); total yield: 72%. Melting point: 220°–221° C. (uncorrected) $R_f$=0.47 (petroleum ether: ethyl acetate=1:1)

EXAMPLE V

Tert-butyl 4-methylphenyl-acetate

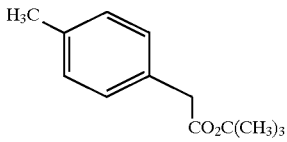

450 g (3 mol) of 4-methylphenyl-acetic acid (Aldrich), 1.13 l (12 mol) of tert-butanol and 90 g (0.74 mol) of 4-(N,N-dimethylamino)pyridine are dissolved in 2 l of methylene chloride. After addition of 680 g (3.3 mol) of dicyclohexylcarbodiimide, dissolved in 400 ml of methylene chloride, the mixture is stirred at 25° C. for 20 hours, the urea which has precipitated out is filtered off with suction and washed with 200 ml of methylene chloride and the organic phase is washed in each case twice with 500 ml of 2M hydrochloric acid and water. The organic phase is concentrated and distilled. Yield: 408 g (66% of theory) Boiling point: 73°–78° C./0.2 mm

EXAMPLE VI

Tert-butyl 2-(R,S)-2-cyclopentyl-2-(4-methylphenyl) acetate

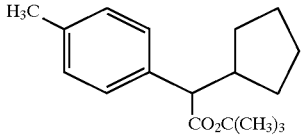

33.5 g (0.3 mol) of potassium tert-butylate are initially introduced into 100 ml of anhydrous DMF at 0° C., and 51.6 g (0.25 mol) of the compound from Example V in 250 ml of anhydrous DMF are added dropwise. The mixture is stirred at 0° C. for 30 minutes, 32.2 ml (0.3 mol) of cyclopentyl bromide in 150 ml of anhydrous DMF are added dropwise at 5°–15° C. and the mixture is stirred at 25° C. for 20 hours. After concentration, the residue is partitioned between water and diethyl ether and the ether phase is dried over sodium sulphate and concentrated. The product crystallizes out. Yield: 67 g (97.5% of theory) Melting point=51°–53° C.

EXAMPLE VII

Tert-butyl 2-(R,S)-2-(4-bromomethyl-phenyl)-2-cyclopentyl-acetate

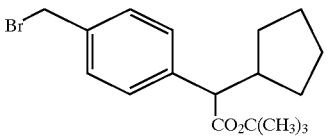

27.4 g (0.1 mol) of the compound from Example VI are dissolved in 200 ml of carbon tetrachloride and the solution is heated to the boiling point. After addition of 0.82 g of azobisisobutyronitrile, 18.7 g (0.105 mol) of N-bromosuccinimide are added in portions, the mixture is then refluxed for 1 hour and cooled to 0° C. and the succinimide is filtered off. After concentration of the filtrate, the product precipitates out. It is washed with petroleum ether (40/60) and dried. Yield: 20 g (57% of theory) Melting point=73°–76° C.

EXAMPLE VIII

Tert-butyl 2-(R,S)-2-cyclopentyl-2-[4-(2,4-dimethyl-α-carbolin-9-yl)methyl]phenyl-acetate

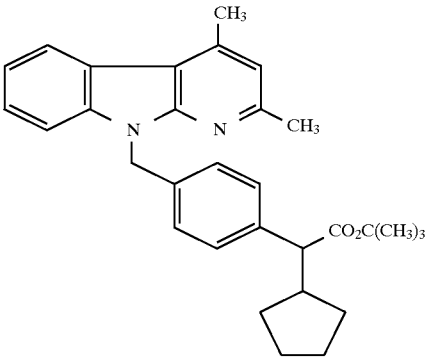

73.6 g (375 mmol) of the compound from Example IV are reacted with 42.13 g (375 mmol) of potassium tert-butanolate in 700 ml of anhydrous N,N-dimethylformamide at 25° C. for 30 minutes, and 161.7 g (375 mmol) of the compound from Example VII, dissolved in 680 ml of anhydrous N,N-dimethylformamide, are then added. After 1 hour, the reaction has ended (monitoring by thin layer chromatography; petroleum ether: ethyl acetate=10:1). For working up, 2 l of buffer solution (pH=4/Merck) and 2 l of water are added, and the precipitate obtained is filtered off with suction, washed with water and filtered under high suction again. The moderately moist solid is now stirred successively with petroleum ether and methanol and filtered off with suction. Drying in vacuo over phosphorus pentoxide gives 139.8 g (298 mmol/79%) of product. Melting point= 160°–161° C. (uncorrected) $R_f$=0.39 (petroleum ether: ethyl acetate=10:1)

EXAMPLE IX 2-(R,S)-2-Cyclopentyl-2-[4-(2,4-dimethyl-α-carbolin-9-yl)methyl]phenylacetic acid hydrochloride

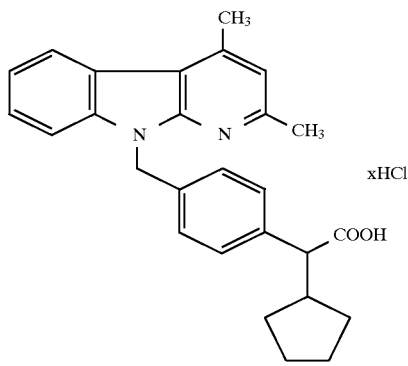

139.8 g (298 mmol) of the compound from Example VIII are dissolved in 1 1 of 1,4-dioxane and the solution is stirred with 240 ml of concentrated hydrochloric acid (37% strength) at 70° C. for 3 hours. When the reaction has ended (monitoring by thin layer chromatography; petroleum ether: ethyl acetate=10:1), the batch is cooled to about 15° C. and then poured in portions onto 5 1 of water. The pH is brought to 2.8 with 2M aqueous sodium hydroxide solution and the precipitate obtained is filtered off with suction over filter paper and rinsed with water until the wash water has a pH >4. The solid is filtered under high suction, stirred with 1 1 of petroleum ether (boiling range 60°–80° C.), filtered off with suction again and dried in vacuo over phosphorus pentoxide. Yield: 130.3 g (290 mmol/97%) Melting point= 260°–262° C. (uncorrected) $R_f$=0.51 (methylene chloride: ethanol=20:1)

Preparation Examples

EXAMPLE 1

9-{4-[1-(R,S1-Amino-1-cyclopentyl-methyl]phenyl-methyl}-2,4-dimethyl-(α-carboline

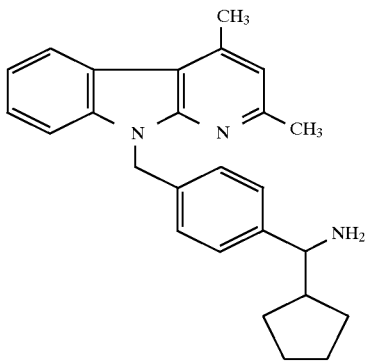

20.0 g (48.5 mmol) of the compound from Example IX are dissolved in 160 ml of anhydrous DMF, and 12.4 ml (58.2 mmol) of phosphoric acid diphenyl ester azide and 16.1 ml (116.4 mmol) of triethylamine are added at 0° C. The reaction mixture is stirred at 70° C. for one hour and cooled to 0° C., 62.5 ml of 6M hydrochloric acid are slowly added and the mixture is stirred at 70° C. for a further 2.5 hours. The batch is poured onto 2 l of water and brought to a pH of 2. The precipitate obtained is filtered off with suction, washed successively with water and petroleum ether, and in each case filtered under high suction. After drying over phosphorus pentoxide under a high vacuum, a crude product is present which, when stirred with methylene chloride, filtered off with suction and dried under a high vacuum, gives 13.6 g (35.5 mmol) of the pure product. $R_f$=0.35 (methylene chloride: ethanol=5:1) MS (FAB): m/z= 384 (49% [M+H]$^+$), 367 (100%, M$^+$-NH$_2$), 314 (31%, M$^+$-cPent).

EXAMPLE 2

9-{4-[1-(R,S)- 1-(2-(R,S)-2-Phenyl-2-ethoxycarbonyl-acetyl)amino- 1-cyclopentyl-methyl]phenyl-methyl }-2,4-dimethyl-α-carboline

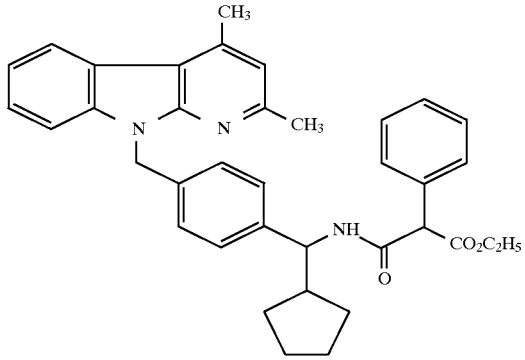

1.1 ml (7.8 mmol) of triethylamine are added to 1.0 g (2.6 mmol) of the compound from Example 1 in 60 ml of methylene chloride, and the mixture is reacted with a solution of 0.89 g (2.7 mmol) of 2-(R,S)-2-phenyl-malonic acid chloride ethyl ester in 5 ml of methylene chloride at 20° C. After 3 hours, buffer (Merck) of pH=4 is added, the phases are separated and subsequent extraction with buffer and water is carried out. The organic phase is dried with magnesium sulphate and evaporated and the resulting residue is purified by chromatography over silica gel 60 (Merck, methylene chloride: ethanol=100:1). Yield: 0.75 g $R_f$=0.32 (methylene chloride: ethanol=50:1) MS (FAB): m/z=596 (11% [M+Na]$^+$), 574 (100%, M+H]$^+$), 504 (9% [M-C$_5$H$_9$]$^+$).

The compounds of Table 1 are prepared analogously to the instructions of Example 2:

TABLE 1

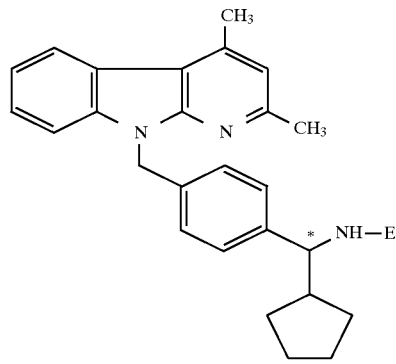

*racemic

| Example No. | —E | $R_f$ (solvent) | MS | Starting material (Example No.) |
|---|---|---|---|---|
| 3 | —SO$_2$CH$_2$C$_6$H$_5$ | 0.56 (B) | | 1 |
| 4 | —CO—CH$_2$C$_6$H$_5$ | 0.25 (B) | | 1 |
| 5 | —CO—CH$_2$—C$_6$H$_4$—OCH$_3$ | 0.27 (B) | | 1 |
| 6 | —CO—CH$_2$—C$_6$H$_4$—OCH$_3$ (meta) | 0.23 (B) | | 1 |
| 7 | *rac CO—CH(C$_6$H$_5$)—OCOCH$_3$ | 0.28 (B) | | 1 |
| 8 | —C(=S)—O—C$_6$H$_5$ | 0.56 (C) | | 1 |
| 9 | —SO$_2$—C$_6$H$_5$ | 0.20 (C) | | 1 |
| 10 | —CO—C$_6$H$_5$ | 0.14 (C) | | 1 |
| 11 | —C(=O)—C$_6$H$_5$ | 0.25 (C) | | 1 |

| Example No. | —E | $R_f$ (solvent) | MS/ MP. | Starting material (Example No.) |
|---|---|---|---|---|
| 12 | —C(=O)—S—C$_6$H$_5$ | 0.55 (B) | | 1 |
| 13 | —CO(CH$_2$)$_2$—C$_6$H$_5$ | 0.40 (A) | | 1 |
| 14 | —CO—CH$_2$—C$_6$H$_3$(Cl)(CH$_3$) | 0.49 (B) | | 1 |

TABLE 1-continued

| | | | | |
|---|---|---|---|---|
| 15 | —CO—CH₂—⟨C₆H₄⟩—Cl | 0.37 (A) | | 1 |
| 16 | —CO—CH₂—⟨C₆H₄⟩—CH₃ | 0.41 (E) | 516 (100%)/ 222° C. | 1 |

EXAMPLE 17

9-{4-[1-(R,S)1-(2-(R,S)-2-Phenyl-2-hydroxymethyl-acetyl)amino-1-cyclopentyl-methyl]phenyl-methyl}-2,4-dimethyl-α-carboline

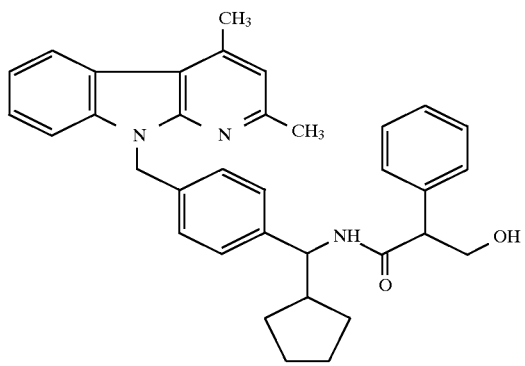

688 mg (1.2 mmol) of the compound from Example 2 are dissolved in 10 ml of THF and are reacted with 2.4 ml (2.4 mmol) of 1M lithium alanate solution in THF at 0° C., the internal temperature being allowed to rise to 20° C. After 4 hours, the reaction has still not ended, a further 1.2 ml (1.2 mmol) of 1M lithium alanate solution in THF are added and the mixture is stirred at 20° C. for a further 3 hours. Thereafter, the mixture is poured onto buffer of pH=4 (Merck) and ethyl acetate, the phases are separated and the aqueous phase is subsequently extracted several times with ethyl acetate. The combined organic extracts are dried with magnesium sulphate and evaporated. The crude product is purified by chromatography over silica gel 60 (Merck, methylene chloride: ethanol=100:1). Yield: 240 mg $R_f$=0.11 (methylene chloride: ethanol=50:1) MS (FAB): m/z=532 (49%, [M+N]⁺).

EXAMPLE 18

9-{4-[1-(R,S)-1-(2-(R,S)-2-Phenyl-2-hydroxy-acetyl)amino-1-cyclopentyl-methyl]phenyl-methyl}-2,4-dimethyl-α-carboline

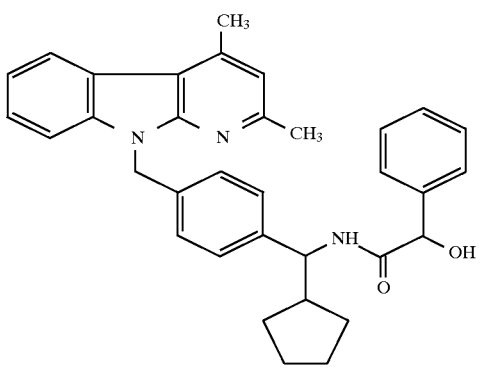

600 mg (1.07 mmol) of the compound from Example 7 are reacted with 10 ml of 2M aqueous sodium hydroxide solution in 10 ml of ethanol at 40° C. for 2 hours. The reaction mixture is diluted with 40 ml of water and slowly brought to a pH of 5.6 with 2M hydrochloric acid at 0° C. The precipitate obtained is filtered off with suction, washed with water and dried under a high vacuum over phosphorus pentoxide. Yield: 485 mg $R_f$=0.63 (methylene chloride: ethanol=20:1) MS (FAB): m/z 540 (28%, [M+Na]⁺), 518 (100%, ([M+H]⁺).

EXAMPLE 19

9-{4-[1-(R,S)- 1 (2-Thienyl-acetyl)amino-1-cyclopentyl-methyl]phenyl-methyl}-2,4-dimethyl-α-carboline

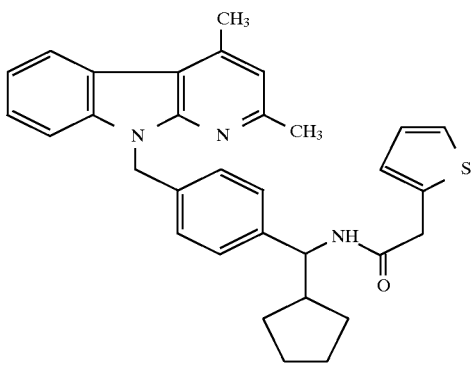

193.7 mg (1.43 mmol) of HOBT, 287.4 mg(1.5 mmol) of N'-(3-dimethylaminopropyl)-N-ethylcarbodiimide hydrochloride, 361 μl (2.61 mmol) of triethylamine and 184.8 mg (1.3 mmol) of thienylacetic acid are added to 500 mg (1.3 mmol) of the compound from Example 1 in 60 ml of methylene chloride at 10° C. and the mixture is stirred for 20 hours, while warning to 20° C. The reaction mixture is extracted several times with hydrochloric acid of pH=4, and then with aqueous ammonium chloride solution, with aqueous sodium bicarbonate solution and with water, dried with solid, anhydrous magnesium sulphate and evaporated. The crude product is stirred with methanol, filtered off with suction, rinsed once more with methanol and dried under a high vacuum over phosphorus pentoxide. Yield: 400 mg $R_f$=0.35 (methylene chloride: ethanol=20:1)

The compounds of Table 2 are prepared analogously to the instructions of Example 19:

TABLE 2

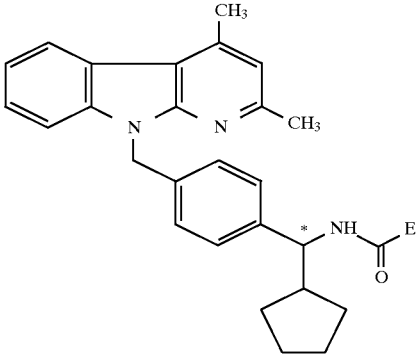

*racemic

| Example No. | E | $R_f$ (solvent) | MS/m.p. | Starting material (Example No.) |
|---|---|---|---|---|
| 20 | 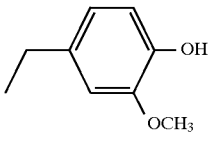 | 0.26 (A) | | 1 |
| 21 | 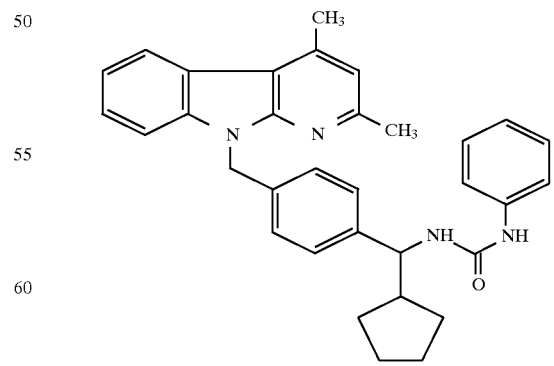 | 0.38 (A) | | 1 |
| 22 | —CO—C$_6$H$_5$ | 0.26 (F) | 516 (35%) | 1 |

EXAMPLE 23

9-{4-[1-(R,S)-1-Phenylaminocarbonylamino-1-cyclopentyl-methyl]phenyl-methyl}-2,4-dimethyl-α-carboline 400 mg (1.04 mmol) of the compound from Example 1 are reacted with 117.6 mg (0.988 mmol) of phenyl isocyanate in 60 ml of anhydrous methylene chloride at 20° C., after addition of 433 μl (3.13 mmol) of triethylamine. After 3 hours, 120 ml of buffer (Merck) of pH=4 are added and the organic phase is washed twice with water, dried with magnesium sulphate and evaporated to dryness. The residue is stirred with methanol, filtered off with suction and washed once again with methanol. Subsequent drying under a high vacuum over phosphorus pentoxide gives 385 mg of product. $R_f$=0.54 (methylene chloride: ethanol=20:1) MS (FAB): m/z=503 (14%, [M+H]$^+$), 307 (100%).

EXAMPLE 24

9-{4-[1-(R,S)-1-(2-(E,Z)-2-hydroxyimino-2-phenyl-acetyl)amino-1-cyclopentyl-methyl]phenyl-methyl}-2,4-dimethyl-α-carboline

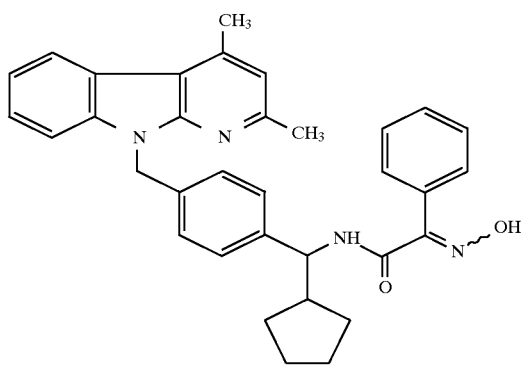

53.9 mg (0.78 mmol) of hydroxylammonium chloride are added to 200 mg (0.39 mmol) of the compound from Example 22 in 10 ml of pyridine and the mixture is boiled under reflux for 20 hours. The cooled reaction mixture is poured onto aqueous buffer (pH=2/Merck) and ether, the phases are separated and the aqueous phase is subsequently extracted several times with ether. Thereafter, the product phase is dried with magnesium sulphate and evaporated. Purification by chromatography (silica gel 60/Merck/ petroleum ether: ethyl acetate=5:1 to 2:1) gives a yield of 135 mg of substance. $R_f$=0.24 and 0.34 (petroleum ether: ethyl acetate=2:1) MS (FAB): m/z=531 (100%, [M+H]$^+$), 367 (32%, M$^+$-NHCOC(Ph)=NOH).

The compounds of Table 3 are prepared analogously to the instructions of Example 24:

TABLE 3

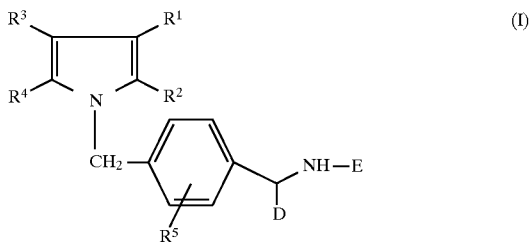

*racemic

| Ex. No. | R$^{17}$ | Isomer | R$_f$ (solvent) | MS-FAB | Starting material Ex. No. |
|---|---|---|---|---|---|
| 25 | —OCH$_3$ | E + Z | 0.28 (B) | 545 (50%) | 22 |
| 26 | —NH—CO—NH$_2$ | E + Z | 0.49/ 0.52 (A) | 573 (100%) | 22 |
| 27 | —NH—CS—NH$_2$ | E + Z | 0.48/ 0.53 (A) | 589 (29%) | 22 |

We claim:
1. An amide or sulphonamide of a benzylamine having a heterocyclic substituent of the formula I,

$$\text{(I)}$$

in which
R$^1$ and R$^2$, including the double bond joining them, together form a pyridyl ring,
R$^3$ and R$^4$, including the double bond joining them, together form a phenyl ring or a cyclopentene, cyclohexene, cycloheptene or cyclooctene radical,
 wherein all the ring systems mentioned under R$^1$/R$^2$ and R$^3$/R$^4$ are substituted by 0–2 members in an identical or different manner selected independently from the group consisting of fluorine, chlorine bromine, trifluoromethyl, carboxyl, hydroxyl or straight-chain or branched alkoxy or alkoxycarbonyl having in each case up to 4 carbon atoms or by straight-chain or branched alkyl having up to 4 carbon atoms, which in its turn can be substituted by hydroxyl or by straight-chain or branched alkoxy having up to 3 carbon atoms,
R$^5$ represents hydrogen, fluorine, chlorine, bromine, trifluoromethyl, carboxyl or straight-chain or branched alkyl, alkoxy or alkoxycarbonyl having in each case up to 4 carbon atoms,
D represents hydrogen, cyclobutyl, cyclopentyl, cyclohexyl, cycloheptyl or cyclooctyl, or represents straight-chain or branched alkyl having up to 7 carbon atoms, E represents hydrogen, or represents a radical of the formula

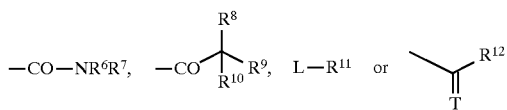

in which
$R^6$ and $R^7$ are identical or different and denote hydrogen, phenyl or straight-chain or branched alkyl having up to 6 carbon atoms,
$R^8$ denotes hydrogen, straight-chain or branched alkyl having up to 6 carbon atoms, phenyl, pyridyl, furyl, thienyl or imidazolyl, which are optionally substituted by 0–2 members in an identical or different manner selected independently from the group consisting of nitro, carboxyl, fluorine, chlorine, bromine or cyano, by straight-chain or branched alkoxycarbonyl having up to 4 carbon atoms or by straight-chain or branched alkyl having up to 5 carbon atoms, which is unsubstituted or substituted by a member selected from the group consisting of hydroxyl, carboxyl or by straight-chain or branched alkoxy or alkoxycarbonyl having in each case up to 5 carbon atoms, and/or the cyclic radicals are unsubstituted or substituted by a group of the formula $—OR^{13}$,
wherein
$R^{13}$ represents hydrogen or straight-chain or branched alkyl or alkenyl having in each case up to 4 carbon atoms,
$R^9$ denotes carboxyl, hydroxyl, straight-chain or branched alkoxycarbonyl having up to 4 carbon atoms or a group of the formula $—CH_2OH$ or $—O—CO—R^{14}$,
  wherein
  $R^{14}$ represents straight-chain or branched alkyl having up to 4 carbon atoms,
$R^{10}$ denotes hydrogen,
or
$R^9$ and $R^{10}$ together form a radical of the formula $=O$ or $=N—R^{15}$,
  wherein
  $R^{15}$ represents hydroxyl, straight-chain or branched alkoxy having up to 4 carbon atoms or a radical of the formula $—NH—CO—NH_2$ or $—NI—CS—NH_2$,
L denotes a group $—SO_2—$ or $—CO—$,
$R^{11}$ denotes phenyl, pyridyl, thienyl, furyl or pyrimidyl or straight-chain or branched alkyl having up to 4 carbon atoms, which is unsubstituted or substituted by a member selected from the group consisting of pyridyl, thienyl, furyl or pyrimidyl, wherein all the ring systems are substituted by 0–2 members in an identical or different manner selected from the group consisting of hydroxyl, phenoxy, fluorine, chlorine or bromine or a straight-chain or branched alkyl or alkoxy having in each case up to 4 carbon atoms,
T denotes a sulphur or oxygen atom and
$R^{12}$ denotes phenoxy, phenylthio or straight-chain or branched alkoxy having up to 4 carbon atoms,
or a salt thereof.

2. An amide or sulphonamide of a benzylamine having a heterocyclic substituent of the formula according to claim 1, in which
$R^1$ and $R^2$, including the double bond joining them, together form a phenyl or pyridyl ring,
$R^3$ and $R^4$, including the double bond joining them, together form a phenyl ring or a cyclopentene, cyclohexene, cycloheptene or cyclooctene radical, wherein all the ring systems mentioned under $R^1/R^2$ and $R^3/R^4$ are substituted by 0–2 members in an identical or different manner selected from the group consisting of fluorine, chlorine, bromine trifluoromethyl, carboxyl or hydroxyl, by straight-chain or branched alkoxy or alkoxycarbonyl having in each case up to 3 carbon atoms or by straight-chain or branched alkyl having up to 3 carbon atoms, which in its turn can be substituted by hydroxyl, methoxy or ethoxy,
$R^5$ represents hydrogen, fluorine, chlorine, bromine, trifluoromethyl, trifluoro-methoxy or methyl,
D represents hydrogen, cyclopentyl, cyclohexyl, cycloheptyl or cyclooctyl, or represents straight-chain or branched alkyl having up to 6 carbon atoms,
E represents hydrogen, or represents a radical of the formula

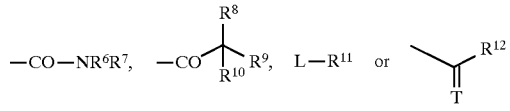

in which
$R^6$ and $R^7$ are identical or different and denote hydrogen, phenyl or straight-chain or branched alkyl having up to 6 carbon atoms,
$R^8$ denotes hydrogen, straight-chain or branched alkyl having up to 6 carbon atoms, phenyl, pyridyl or thienyl, which are substituted by 0–2 members in an identical or different manner independently selected from the group consisting of nitro, carboxyl, fluorine, chlorine, bromine or cyano, by straight-chain or branched alkoxycarbonyl having up to 3 carbon atoms or by straight-chain or branched alkyl having up to 4 carbon atoms, which is unsubstituted or substituted by hydroxyl or carboxyl or by straight-chain or branched alkoxy or alkoxycarbonyl having in each case up to 4 carbon atoms, and/or the cyclic radicals are unsubstituted or substituted by a group of the formula $—OR^{13}$
  wherein
  $R^{13}$ represents hydrogen or straight-chain or branched alkyl or alkenyl having in each case up to 3 carbon atoms,
$R^9$ denotes carboxyl, hydroxyl, straight-chain or branched alkoxycarbonyl having up to 3 carbon atoms or a group of the formula $—CH_2OH$ or $—O—CO—R^{14}$,
  in which
  $R^{14}$ represents straight-chain or branched alkyl having up to 3 carbon atoms,
$R^{10}$ denotes hydrogen,
or
$R^9$ and $R^{10}$ together form a radical of the formula $=O$ or $=N—^{15}$,
  wherein
  $R^{15}$ denotes hydroxyl, straight-chain or branched alkoxy having up to 3 carbon atoms or a radical of the formula $—NH—CO—NH_2$ or $—NH—CS—NH_2$,
L denotes a radical of the formula $—SO_2$ or $—CO$,
$R^{11}$ denotes phenyl, pyridyl or thienyl or straight-chain or branched alkyl having up to 3 carbon atoms, which is unsubstituted or substituted by phenyl, pyridyl or thienyl, wherein all the ring systems are substituted by 0–2 members in an identical or different manner selected independently from the group consisting of hydroxyl, phenoxy, fluorine, chlorine or bromine or by straight-chain or branched alkyl or alkoxy having in each case up to 3 carbon atoms,
T denotes a sulphur or oxygen atom and
$R^{12}$ denotes phenoxy, phienylthio or straight-chain or branched alkoxy having up to 3 carbon atoms,
or a salt thereof.

3. A composition for the treatment of atherosclerosis comprising an amount effective therefor of a compound or a salt thereof according to claim 1 and a pharmacologically acceptable diluent.

4. The method of treating atherosclerosis in a patient in need thereof which comprises administering to such patient an amount effective therefor of a compound or a salt thereof according to claim 1.

5. A compound according to claim 1, wherein such compound is 9-{4-[1-(R/S)-1-Cyclopentyl-1-(phenyl-acetyl-amino)-methyl]-phenyl-methyl)}-2,4-dimethyl-α-carboline of the formula

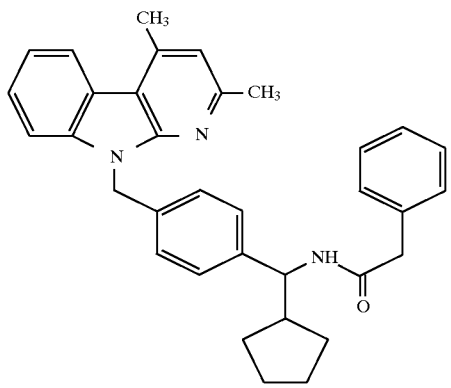

or a salt thereof.

6. A compound according to claim 1, wherein such compound is 9-{4-[1-(R/S)-1-Cyclopentyl-1-([4-methoxy-phenyl]-acetyl-amino)-methyl]-phenyl-methyl}-2,4-dimethyl-α-carboline of the formula

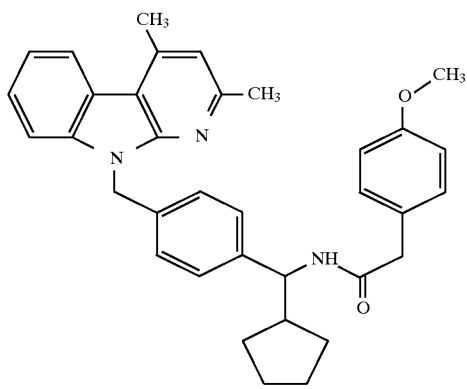

or a salt thereof.

7. A compound according to claim 1, wherein such compound is 9-{4-[1-(R/S)-1-Cyclopentyl-1-([4-chlor-phenyl]-acetyl-amino)-methyl]-phenyl-methyl}-2,4-dimethyl-α-carboline of the formula

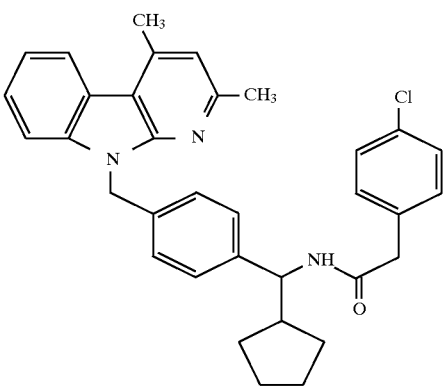

or a salt thereof.

8. A compound according to claim 1, wherein such compound is 9-{4-[1-(R/S)-1(2-(R/S)-2-Phenyl-2-hydroxy-acetyl))amino-1-cyclopentyl-methyl]phenyl-methyl}-2,4-dimethyl-α-carboline of the formula

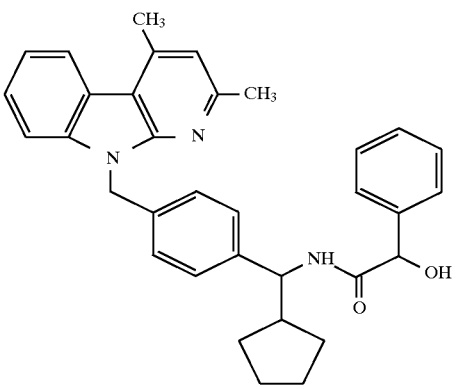

or a salt thereof.

9. A compound according to claim 1, wherein such compound is 9-{4-[1-(R/S)-1-Cyclopentyl-([3-pyridyl]-acetyl-amino)-methyl)-phenyl-methyl}-2,4-dimethyl-α-carboline of the formula

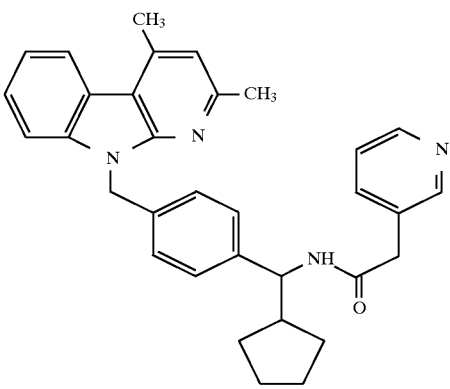

or a salt thereof.

* * * * *

UNITED STATES PATENT AND TRADEMARK OFFICE
CERTIFICATE OF CORRECTION

PATENT NO. : 5,849,751
DATED : December 15, 1998
INVENTOR(S) : Muller, et al.

It is certified that error appears in the above-indentified patent and that said Letters Patent is hereby corrected as shown below:

Col. 29, line 43　Delete " $NI-CS-NH_2$ " and substitute -- $NH-CS-NH_2$ --

Col. 29, line 48　After " consisting of " insert -- phenyl --

Col. 30, line 48　Delete " $=N-^{15}$ " and substitute -- $=N-R^{15}$ --

Col. 30, line 63　Delete " phienylthio " and substitute -- phenylthio --

Signed and Sealed this

Twenty-ninth Day of June, 1999

Attest:

Q. TODD DICKINSON

*Attesting Officer*　　*Acting Commissioner of Patents and Trademarks*